United States Patent [19]

Vrana et al.

[11] 4,038,975

[45] Aug. 2, 1977

[54] METHOD OF AND APPARATUS FOR THE DETECTOR OF NEOPLASMS AND OTHER MORPHOLOGIC CHANGES IN MUCOUS MEMBRANE SAMPLES

[75] Inventors: Jiri Vrana; Jaroslav Setka, both of Prague, Czechoslovakia

[73] Assignee: Vyvojova a provozni zakladna vyzkumnych ustavu, Bechovice, Czechoslovakia

[21] Appl. No.: 610,422

[22] Filed: Sept. 4, 1975

Related U.S. Application Data

[63] Continuation-in-part of Ser. No. 488,402, July 15, 1974, abandoned.

[51] Int. Cl.² .............................................. A61B 5/05
[52] U.S. Cl. ............................ 128/2.1 Z; 324/57 R; 324/62
[58] Field of Search ............ 128/2.1 Z, 2.1 R, 2.1 E; 324/57 R, 62 R

[56] References Cited

U.S. PATENT DOCUMENTS

| 2,184,511 | 12/1939 | Bagno et al. | 128/2.1 Z |
| 3,048,775 | 8/1962 | Calvert | 324/62 R |
| 3,064,641 | 11/1962 | Manenti et al. | 128/2.1 R |
| 3,085,566 | 4/1963 | Talles | 128/2.1 Z |
| 3,316,896 | 5/1967 | Thomassett | 128/2.1 Z |
| 3,949,736 | 4/1976 | Vrana et al. | 128/2.1 Z |

OTHER PUBLICATIONS

Geddes et al., "Measurement of Phys. Events by Elec. Imp.", The Am. J. Med. Elec., Jan.-Mar. 1964, pp. 16-27.
Kaysey et al., "Ident. of Cond. Tissue of Heart," Am. J. Med. Elec., Apr.-June 1963, pp. 120-124.

*Primary Examiner*—Robert W. Michell
*Assistant Examiner*—Lee S. Cohen

[57] ABSTRACT

A living specimen of a mucous membrane tissue is connected in series with a high-frequency voltage generator and a pair of like-valued resistors. The bulk of the membrane sample is connected via a larger-area contact to the grounded terminal of the generator, while a test spot of the membrane sample is connected via a small-area contact to the terminal of one of the resistors remote from its junction with the other resistor. Measurement of the potential at the test spot and at two other points of the circuit are simultaneously made, and are evaluated in an analog computer or other suitable facilities to derive therefrom the real and imaginary parts of the potential at the test spot of the membrane sample. The relative amplitudes of the real and imaginary components are indicative of the presence or absence of a neoplasm.

5 Claims, 4 Drawing Figures

METHOD OF AND APPARATUS FOR THE DETECTOR OF NEOPLASMS AND OTHER MORPHOLOGIC CHANGES IN MUCOUS MEMBRANE SAMPLES

CROSS-REFERENCE TO RELATED APPLICATIONS

This application is a continuation-in-part of applicants' now abandoned application Ser. No. 488,402 filed July 15, 1974 and entitled CIRCUIT ARRANGEMENT FOR DETERMINING CHANGES OF IMPEDANCE OF BIOLOGICAL OBJECTS, PARTICULARLY OF TISSUES.

BACKGROUND OF THE INVENTION

The invention concerns an electrically-instrumented technique of diagnosing the presence of a neoplast in a mucous membrane sample.

The response of a live sample of mucous membrane to alterating current is typically that of an R-C circuit whose resistive portion is determined by the properties of the intercellular liquid and whose capacitive portion corresponds to the diaphragm capacitance of all the cells in the sample, arranged in a series of layers between the electrodes which supply the alternating current to the sample. The diaphragm capacitance, especially, has extraordinary physiological importance. Other equivalent electrical components exist in such sample, but they can be neglected, particularly when the current flow through the sample is negligible.

It has been experimentally determined that changes in the electrical impedance of a membrane sample are indicative of morphologic changes in such sample, such as the presence of neoplasms. Accordingly, circuitry has been developed in the prior art for measuring the absolute value of the voltage across the test sample when such sample is supplied by current via an amplitude-modulated generator and one or more resistors. Unfortunately, since such impedance component is made up of resistive and capacitive portions (i.e., real and imaginary parts of the measured impedance), a relatively large change in one of the components of the measured voltage would have to take place before a statistically significant change in the total measured voltage across the test sample can be measured and evaluated, so that the resulting apparatus is relatively insensitive.

SUMMARY OF THE INVENTION

The technique of the present invention is adapted to directly derive the relative values of the real and capacitive portions of the voltage across a mucous membrane sample, so that changes in such relative values that are too small to be detected with the use of conventional apparatus that measures the resultant voltage changes across the test sample can be picked up. As a result, the formation of neoplasms in healthy tissue can be detected in its infancy, and the chances of a cure are proportionally greater.

Illustratively, the mucous membrane sample to be measured is associated with the terminals of a series circuit which includes, in succession, a grounded amplitude-modulated highfrequency generator whose repetition rate is of the order of 100,000 Hz, and first and second equal-valued resistors. The impedance of the series circuit connected to the membrane sample is low relative to the sample impedance.

A test spot on the sample is coupled via a small-area electrode to the terminal of the second resistor remote from the junction of the first resistor. The bulk of the membrane sample is connected to a ground terminal of the high-frequency generator. Because of the relatively small-area contact to the test spot, taken together with the low output impedance of the series circuit connected to the spot, the potential of such spot is rendered insensitive to changes in the impedance of the circuit.

The amplitudes of the potentials at the test spot and at the junction of the first and second resistors are simultaneously measured with respect to a reference value established at the junction of the generator and the first resistor. The values of such three voltages are then employed in an analog computer or other suitable means to derive the resistive and capacitive portions of the potential at the test spot itself, for the purposes indicated above.

A feature of the invention is an auxiliary circuit for automatically measuring and recording the values of the potential at the test spot and at the junction of the first and second resistors. The circuit includes a first comparator which has a first input connected to the junction of the generator and the first resistor. A second input of the comparator is coupled to a reference voltage, to which the voltage at such last-mentioned junction is to be adjusted. Upon the coincidence of such two voltages, a clock voltage source is turned on to enable a pair of gates which couple the voltages at the junction of the first and second resistors and at the test spot, respectively, to first and second recording means via an additional pair of comparators. Each of the recording means comprises a digital counter, and when the clock generator has stepped each counter to a value corresponding to the digital equivalent of the voltages then on the associated terminals of the series circuit, the respective comparators are disabled to stop the count. The analog equivalents of the then-occurring counts at the outputs of the first and second recording means are thereupon coupled, together with the above-mentioned reference voltage, to an analog computer to derive the real and imaginary portions, respectively, of the voltage at the output of the second recording means.

BRIEF DESCRIPTION OF THE DRAWING

The invention is further set forth in the following detailed description taken in conjunction with the appended drawing, in which.

DETAILED DESCRIPTION

Figure 1:
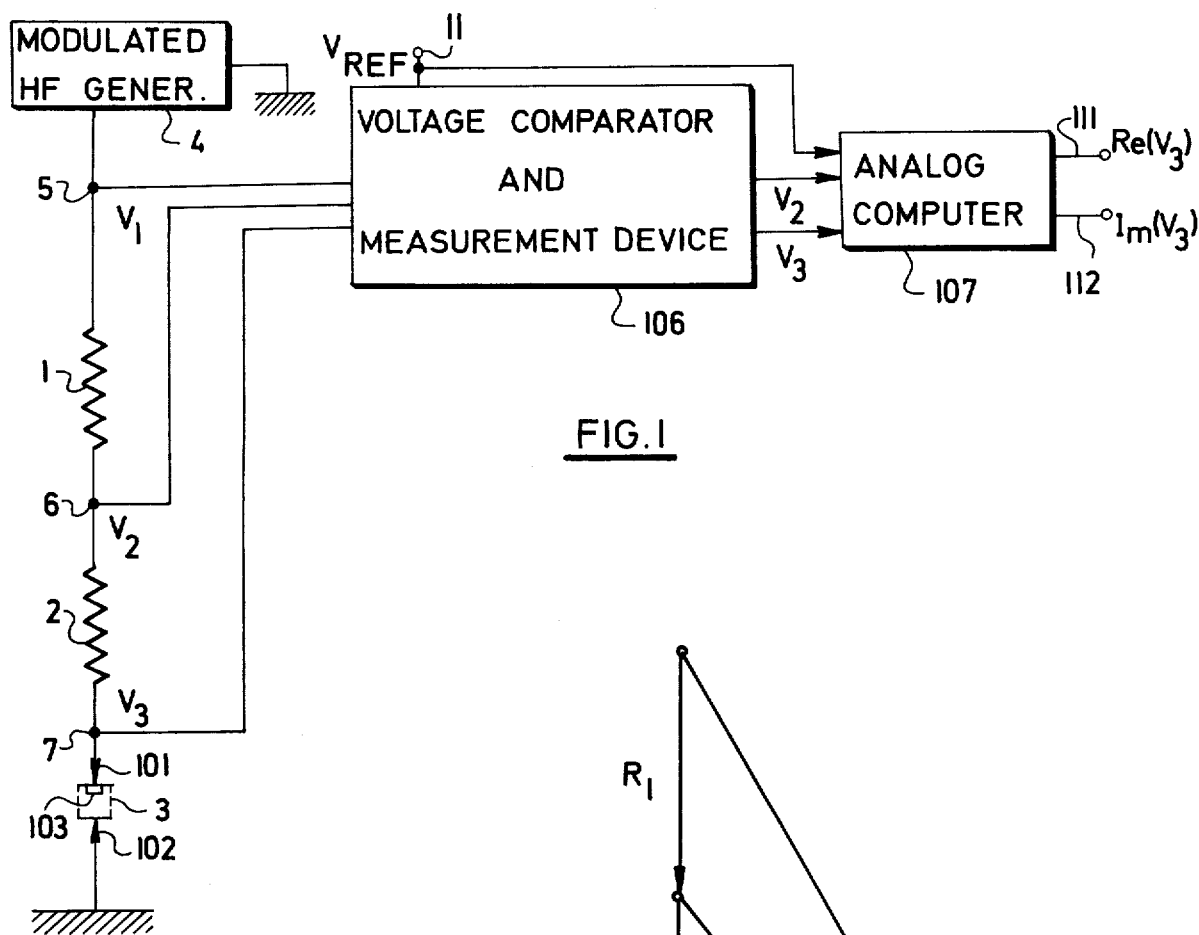
FIG. 1 is a combined block and schematic diagram of an overall electrical arrangement for deriving the real and capacitive portions of the impedance of a measured sample of a mucous membrane.

Referring now to the drawing, FIG. 1 illustrates a circuit suitable for carrying out the technique of the invention for deriving the resistive and capacitive components of the electrical impedance of a mucous membrane sample 3 to determine the presence or absence of a neoplast therein. The sample 3 is connected, via electrode contacts 101 and 102 described below, across a series circuit in which a high-frequency, amplitude modulated generator 4 is serially connected with a pair of successive equal-valued resistors 1 and 2. The output impedance of the generator 4, which is grounded as shown, and the resistances of the individual resistors 1 and 2 are all chosen so that the series circuit impedance connected with the sample 3 is cumulatively much lower than the impedance of the sample. Additionally, it is assumed that the amplitude of the signal at the output of the generator 4 is chosen sufficiently low such that a negligible current (i.e., on the order of 1 microamp) flows through the sample 3 to avoid the generation of spurious components in the equivalent impedance of the sample. The repetition frequency of the generator 4 is chosen to be extremely high, e.g., in the order of 100,000 Hz.

The manner of connection of the sample 3 to the generator 4 is important. As shown, a test spot 103 of the tissue 3 is contacted by the electrode 101, which in turn is connected to a terminal 7 of the resistor 2 remote from its junction 6 with resistor 1. Additionally, the contact 102, connected to the bulk of the sample 3, is coupled to the ground terminal of the generator 4.

Figure 2:
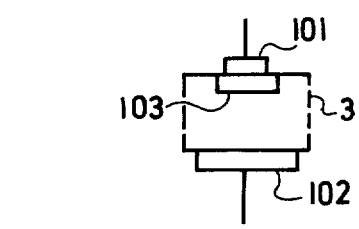
FIG. 2 is a diagrammatic representation of the electrode contacts to the membrane sample in the arrangement of FIG. 1.

As shown best in FIG. 2, the electrode 101 establishes a relatively small-area contact with the test spot 103. By contrast, the grounded electrode 102 establishes a relatively large-area contact with the bulk of the sample 3. It can be shown that the disparity in area of the contacts 101 and 102 serves to insulate the potential at the test point 103 from the effect of impedance changes in the external circuit. It will be understood in this connection that, although the conductors 101 and 102 have been shown as making contact to opposite sides of the specimen 3, such conductors 101 and 102 can respectively form the inner and outer conductors of a conventional coaxial cable with the same advantages.

Figure 3:
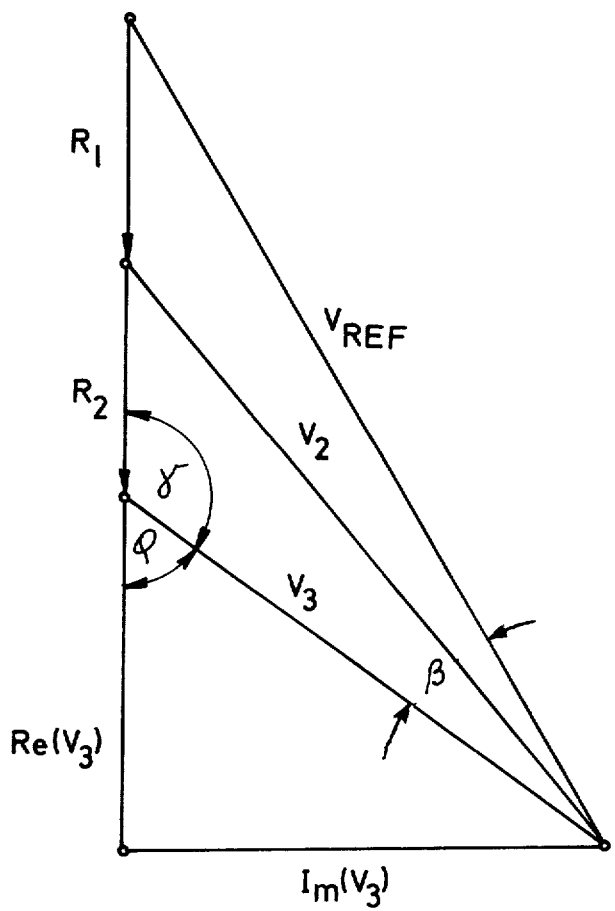
FIG. 3 is a vector diagram illustrating the manner of processing of signals in the analog computer of FIG. 1.

The voltage picked up at the terminal 7 associated with the test point 103 is coupled to a first input of a voltage comparator and measurement device 106 (FIG. 1). In like manner, the potentials at the junction 5 between the generator 4 and the first resistor 1, and the junction 6 between the resistors 1 and 2 are likewise connected to the device 106. Such device 106 responds to the three tapped-off potentials, and to a reference voltage suitably applied via a terminal 11, such that when the voltage $V_1$ present at terminal 5 coincides with the reference voltage at terminal 11, voltages $V_2$ and $V_3$ respectively present at the terminals 6 and 7 at the time of such coincidence are gated to the imput of an analog computer 107. Additionally, the reference voltage, and thereby the voltage $V_1$ at junction 5, is also applied to an input of the analog computer. The computer 107 may be of a conventional construction which is adapted to carry out the vector-type operation which is set forth in detail in FIG. 3. In particular, vectors representing the three input values $V_{ref}$, $V_2$ and $V_3$ are suitably processed to yield at the outputs of such computer, quantities proportional to the real part and imaginary part, respectively, of the measured value $V_3$.

In particular, the analog computer is adapted to resolve the reference voltage $V_{ref}$ into a real portion, including equal vectors $R_1$ and $R_2$ representing the voltage drops across the equal-valued resistors 1 and 2 and the real part of the voltage $V_3$, and an imaginary part represented solely by the imaginary part of $V_3$. The required trigonometric relations in this connection can be represented as follows:

$$\gamma = \cos^{-1}\left[\frac{R^2 + V_3^2 - V_{ref}^2}{2RV_3}\right]$$

$$R = R_1 + R_2$$

$$\phi = \pi - \gamma$$

$$Re(V_3) = V_3 \cos \phi$$

$$Im(V_3) = V_3 \sin \phi$$

The desired calculated values of Re($V_3$) and Im($V_3$) are present at output terminals 111 and 112, respectively, of the computer 107.

Figure 4:
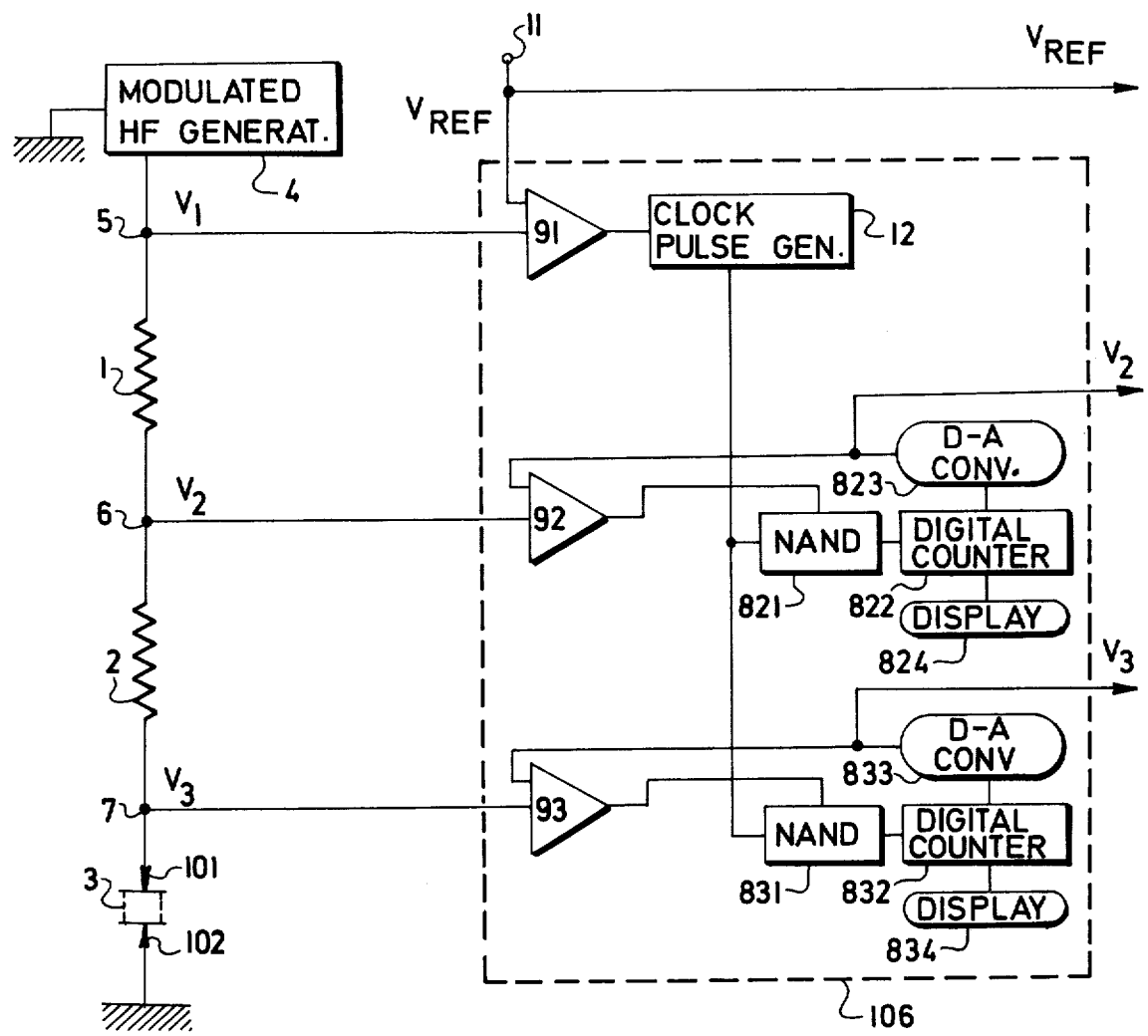
FIG. 4 is a detailed block and schematic diagram of one embodiment of voltage comparator and measurement device of FIG. 1.

One illustrative embodiment of the voltage comparator and measurement device 106 is shown in digital form in FIG. 4. A comparison between the voltage $V_1$ at the terminal 5 and the reference voltage at terminal 11 is accomplished in a conventional comparator 91. Upon the coincidence of the voltage at terminal 5 and the reference voltage at terminal 11 (which may be preset, e.g., at 4 MV), the comparator 91 outpulses a trigger which starts the running of a clockpulse generator 12. The generator 12 is coupled to like first terminals of a pair of NAND gates 821 and 831. During the time that the gates 821 and 831 remain uninhibited, the successive pulses from the clockpulse generator 12 serve to step the appropriate counting inputs of a pair of digital counters 822 and 832, respectively. The counter 822 continues to step until its accumulated count represents the then-occurring value $V_2$ at the terminal 6, which is coupled to the first input of a second comparator 92. As soon as the count in the counter 822, as translated into analog form by an associated digital-to-analog converter 823 reaches a value that coincides with the value $V_2$ at the terminal 6, the comparator 92 is actuated, via a feedback connection to a second input thereof from the converter 823, to apply an inhibiting pulse to the NAND gate 821, thereby preventing a further stepping of the counter 822. The final count in such counter 822 is read out on a suitable digital display 824.

In like manner, the counter 832 is stepped by the generator 12 through the gate 831 until the value of the count established in such counter 832, converted to analog form at the output of a digital-to-analog converter 833, coincides with the voltage $V_3$ present at the junction 7 and thereby at the test region 103 of the sample 3. Since, by analogy to the comparator 92 associated with the terminal 6, the voltage $V_3$ at terminal 7 is applied to a first terminal of a comparator 93 while the output of the digital-to-analog converter 833 is applied to a second input of such comparator 93, a coincidence of the voltage $V_3$ with the analog equivalent of the count established in the counter 832 will be effective to cause the counter 93 to yield an inhibiting signal which is applied to the NAND gate 831, thereby isolating the counter 832 from the pulse generator 12 and stopping the count. The last-mentioned count, corresponding to the voltage $V_3$, is read-out on an associated digital display 834. Since, upon the inhibiting of the gates 821 and 831 the analog outputs of the converters 823 and 833 individually correspond to the values $V_2$ and $V_3$ as indicated above, such outputs are applied to the appropriate inputs of the analog computer 107 to be compared with the reference voltage $V_{ref}$ present at the terminal 11 in the manner indicated above.

In the foregoing, the technique of the invention, and an illustrative arrangement for carrying out such technique, have been set forth. Many variations and modifications will now occur to those skilled in the art. It is accordingly desired that the scope of the appended claims not be limited to the specific disclosure herein contained.

What is claimed is:

1. In an electrically instrumented method of diagnosing the presence of a neoplast in a mucous membrane sample wherein the electrical impedance of the sample has resistive and capacitive components and wherein the relative values of said components are indicative of the presence or absence of said neoplast, the steps of associating the sample with the terminals of a series circuit including in succession a grounded, amplitude-modulated high-frequency generator and first and second equal-valued resistors wherein the impedance of the generator and the resistance of both resistors are low relative to the impedance of the sample, said association being made by connecting a test spot on the sample to the terminal of the second resistor remote from the junction of the first and second resistors and by connecting the bulk of the sample to the grounded terminal of the generator, simultaneously measuring the amplitudes of the potentials of the test spot and of the junction of the first and second resistors with respect to a reference value established at the junction of the generator and the first resistor, and computing from the measured values and from the reference value the resistive and capacitive portions of the potential of the test spot.

2. A method as defined in claim 1, in which the connecting steps are accomplished with a relatively smallarea contact at the test spot and a relatively large-area contact at the sample bulk.

3. A method as defined in claim 1, in which the repetition frequency of the generator is in the order of 100,000 Hz.

4. In an apparatus for the automatic measurement of values proportional to the impedance of a mucous membrane sample, a series circuit comprising in succession a grounded, amplitude-modulated high-frequency generator and first and second equal-valued resistors, the total impedance of the series circuit being low relative to that of the sample, a relatively small-area contact associated with the terminal of the second resistor remote from the first resistor, a relatively largearea contact associated with the grounded terminal of the generator, the sample adapted to be connected between the relatively small-area contact and the relatively large-area contact, a first comparator having a first input connected to a first junction of the generator and the first resistor and a second input connected to a reference voltage, a clock voltage generator having a triggering input connected to the output of the first comparator, second and third comparators individually having first inputs connected to a second junction of the first and second resistors and a third junction of the second resistor and the relatively small-area contact, respectively, first and second means for recording the values of voltages at the second and third junctions, first and second gate means having outputs individually connected to the inputs of the first and second recording means, respectively, the first and second gate means further having first inputs individually connected to the outputs of the second and third comparators, respectively, and second inputs connected to the output of the clock voltage generator, and feedback means for individually coupling the outputs of the first and second recording means to second inputs of the second and third comparators, respectively.

5. Apparatus as defined in claim 4, further comprising analog computing means responsive to the reference voltage and to the output voltages of the first and second recording means for deriving the real and imaginary parts of the output voltage at the third junction.

* * * * *